June 18, 1940. F. B. ABRAMS Plant Pat. 403
ROSE PLANT
Filed Jan. 26, 1940
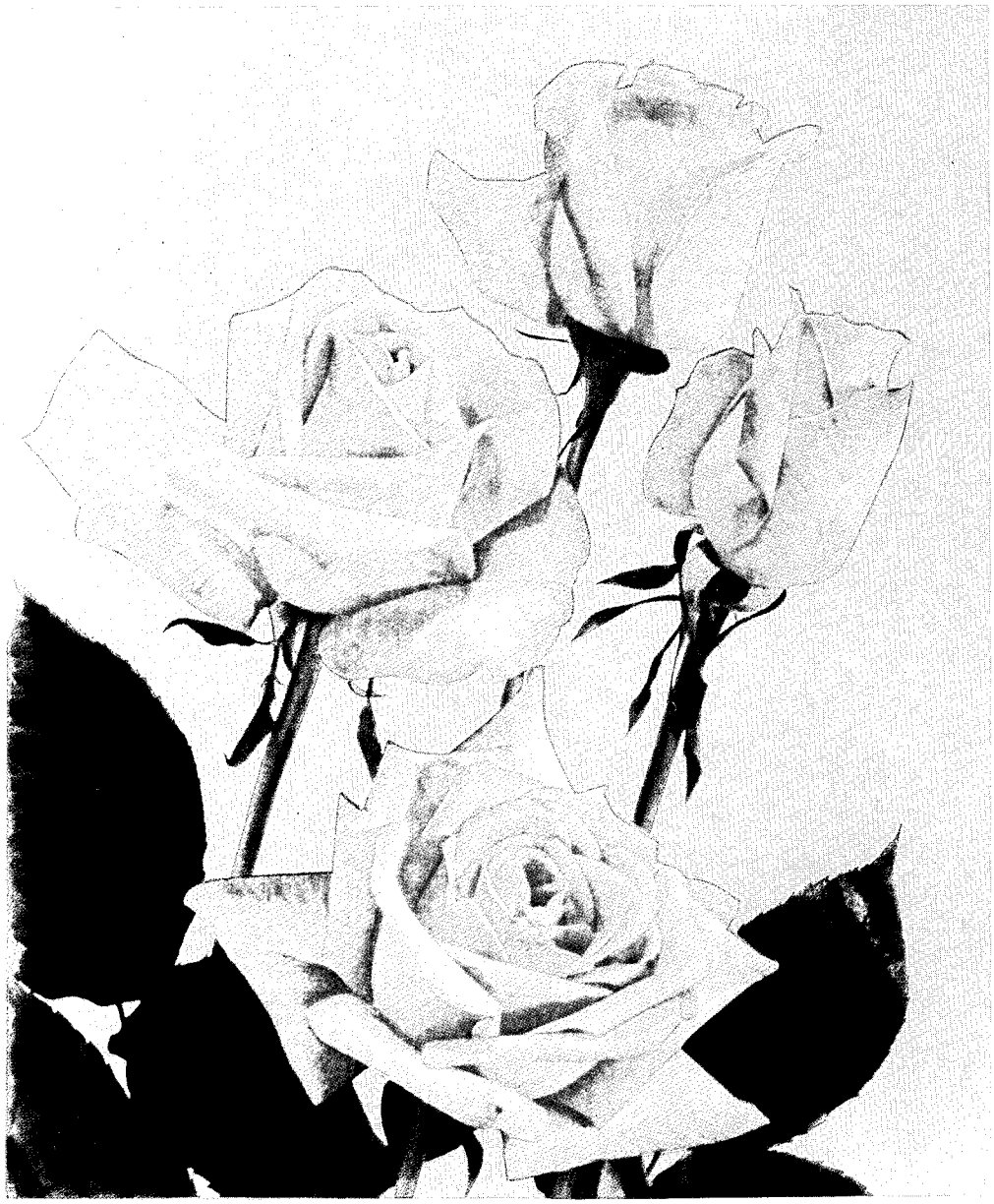
INVENTOR
Fremont Bernard Abrams
By Orville M. Kile
Plant Patent Agt Patented June 18, 1940

Plant Pat. 403

UNITED STATES PATENT OFFICE

403

ROSE PLANT

Fremont Bernard Abrams, Ossining, N. Y.

Application January 26, 1940, Serial No. 315,816

1 Claim. (Cl. 47—61)

My new discovery relates to improvements in hybrid tea roses and pertains particularly to differences in color and size of its blossoms and foliage as compared with those of its parent. The bud of my new variety is much longer than that of its parent; the blossoms of the new variety are larger with greater petalage and have a distinctive lighter color; and the foliage of my new variety is darker and larger.

The new variety is a sport of Better Times and was discovered by me as a branch growing from a Better Times plant in my greenhouses situated at Blue Point, N. Y. It has been asexually reproduced for several years and its characteristics have proved to be permanent.

The original illustrations accompanying this application show four specimen blossoms of my new rose in various stages of opening and in approximately their true colors. It must be understood, however, that it is impossible for the artist to adequately show the velvety brilliance which is a feature of this rose.

Following is a detailed description of my new variety of rose, color designations being in accordance with Ridgway's Color Standards and Nomenclature.

*The plant*

Growth habits: Upright bush with long, strong stems. Growth about the same as that of its parent.

Blooming habit: Continuous and prolific bloomer.

Foliage: Leaves compound, with 3 to 5 leaflets.

*Leaflets.*—*Size*—large, the terminal leaflet being 3¼ to 4 inches long by 1⅝ to 2 inches wide. *Color*—dark, approximately Empire Green (Plate XXXII) on upper surface. Under surface much lighter green. *Shape*—ovate with acuminate apex. *Edge*—sharply serrate. *Texture*—moderately heavy.

*Rachis.*—Short; grooved above; small spine occasionally found on under side. Upper side often has a slight tinge of Deep Hellebore Red (Plate XXXVIII).

*Stipules.*—Narrow; clinging, except the long, acute points.

Stems: Long; strong; Cerro Green (Plate V). Few thorns.

*Thorns.*—None on peduncle. Few on stems. Those appearing are downward pointing, soft light green which turns to Chestnut Brown (Plate XIV) as the rose develops.

*The flower*

Bud:

*Shape.*—Long; urn-shaped; longer than bud of parent variety.

*Size.*—Large.

*Color.*—Between Rose Red and Rose Color (Plate XII).

*Aspect.*—Dull surface; color almost uniformly distributed.

*Opening.*—Slow and in the characteristic Briarcliff manner of the first petal extending at right angles to the rest of the bud.

*Peduncle.*—Long; smooth; straight; approximately Parrot Green (Plate VI).

Blossom:

*Size.*—Large from 4 to 5 inches across when fully expanded.

*Form.*—Very full. Pointed and high-centered, opening into cup shape but still retaining its high center. Outer petals loosely roll backward at top.

*Color.*—The inside of the petals is a rich velvety Rose Red (Plate XII); outside is slightly lighter, falling between Rose Red and Rose Color (Plate XII), and is silky rather than velvety. In cooler weather or after being cut and placed on ice for two or three days, the color is somewhat darker and it then is approximately Tyrian Rose (Plate XII). In both instances the outer surface of the petals is dull and silky while the inner surface has a deep rich velvety brilliance, which cannot be adequately shown in the illustrations or described by reference to the Color Guide.

The color is almost uniformly distributed over the outer surface of the petal but there is a lighter area at the base of the inner surface. Under normal conditions the true color of this rose is retained for several days after being cut.

*Petalage.*—Very double. In the month of December the number of petals averages about 45. The year-round range as observed by me is from 40 to 53 petals.

*Petals.*—*Size*—outer petals very large, measuring up to 2½ inches laterally by 2 inches longitudinally. *Shape*—outer petals broadly obovate, nearly round; usually with sharp point at top; deeply cupped. Inner petals are proportionately narrower but also deeply cupped. As the flower opens the outer petals loosely roll backward, sometimes making the petal straight across the top and sometimes triangular. *Texture*—substantial. *Appearance*—velvety on inner surface; dull on outer surface.

*Fragrance.*—Very profuse and lasting.

*Behavior.*—Petals cling closely.

*Longevity.*—Excellent keeper as cut flower. Normally there is no apparent fading or change of color for several days after being cut.

*Reproductive organs*

Pistils: Many; bunched.

*Styles.*—Medium and irregular lengths; white.

*Stigmas.*—Hellebore Red (Plate XXXVIII) with tip of Naples Yellow (Plate XVI).

Stamens: Many; surround bunched pistils.

*Filaments.*—Rose Red to Pomegranate Red (Plate XII).

*Anthers.*—Large; attached by one end; Apricot Yellow (Plate IV) on edges, with shadings of Hellebore Red in the center and on the under side.

Calyx: Nearly funnel shaped; same color as peduncle.

*Sepals.*—Five; somewhat inclined to be foliaceous; longer than those of its parent; curl backward about peduncle.

Having thus disclosed my discovery, I claim:

The new and distinct variety of hybrid tea rose plant with qualities in combination substantially as shown and described, characterized particularly by its very dark, large foliage; its strong stems; its long urn-shaped bud; and its blossoms having unusually good keeping qualities, a large number of large-sized petals, profuse and lasting fragrance, and brilliant velvety color from Rose Color to Rose Red which is rather evenly distributed over the petal surface and normally does not fade or change for several days.

FREMONT BERNARD ABRAMS.